United States Patent [19]

Wilk

[11] Patent Number: 5,429,144
[45] Date of Patent: * Jul. 4, 1995

[54] CORONARY ARTERY BY-PASS METHOD

[76] Inventor: Peter J. Wilk, 185 W. End Ave., New York, N.Y. 10023

[*] Notice: The portion of the term of this patent subsequent to Feb. 22, 2011 has been disclaimed.

[21] Appl. No.: 222,964

[22] Filed: Apr. 5, 1994

Related U.S. Application Data

[63] Continuation-in-part of Ser. No. 147,072, Nov. 3, 1993, which is a continuation-in-part of Ser. No. 969,747, Oct. 30, 1992, Pat. No. 5,287,861.

[51] Int. Cl.⁶ .............................................. A61B 17/00
[52] U.S. Cl. ........................................ 128/898; 600/16
[58] Field of Search .............................. 128/897–898, 128/672–673, 748, 772, 774; 604/96, 100, 104; 600/16–18; 606/7

[56] References Cited

U.S. PATENT DOCUMENTS

| | | | |
|---|---|---|---|
| 3,995,617 | 12/1976 | Watkins et al. | 600/16 |
| 4,546,499 | 10/1985 | Possis et al. | 623/1 |
| 4,562,597 | 1/1986 | Possis et al. | 623/1 |
| 4,861,330 | 8/1989 | Voss | 600/18 |
| 4,953,553 | 9/1990 | Trimulis | 128/673 |
| 4,985,014 | 1/1991 | Orejola | 600/16 |
| 4,995,857 | 2/1991 | Arnold | 600/16 |
| 5,143,093 | 9/1992 | Sahota | 128/898 |
| 5,190,058 | 3/1993 | Jones et al. | 128/898 |
| 5,287,861 | 2/1994 | Wilk | 128/898 |

*Primary Examiner*—Angela D. Sykes
*Attorney, Agent, or Firm*—R. Neil Sudol; Henry D. Coleman

[57] ABSTRACT

A stent is disposed in the myocardium so that it extends only in the myocardium. The stent may extend only partially through the myocardium, from the left ventricle of the heart or from a coronary artery, upstream of a vascular obstruction. Alternatively, the stent may extend completely through the myocardium to establish a blood flow path from the left ventricle to a coronary artery, downstream of a vascular obstruction.

24 Claims, 5 Drawing Sheets

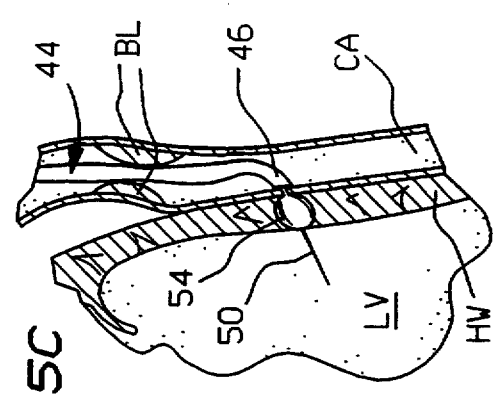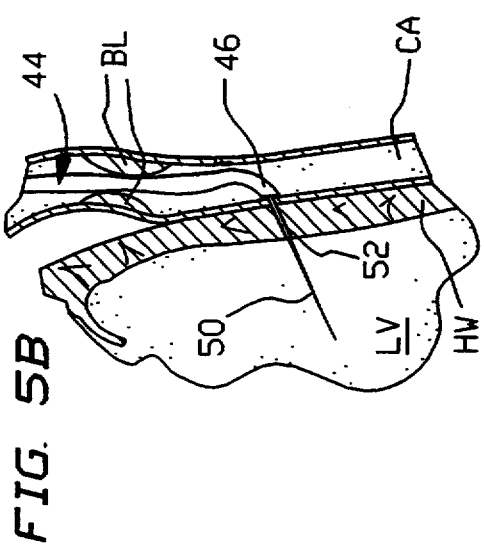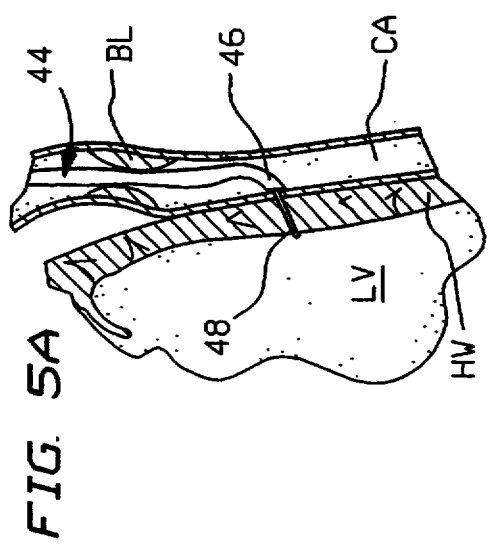
FIG. 5A  FIG. 5B  FIG. 5C
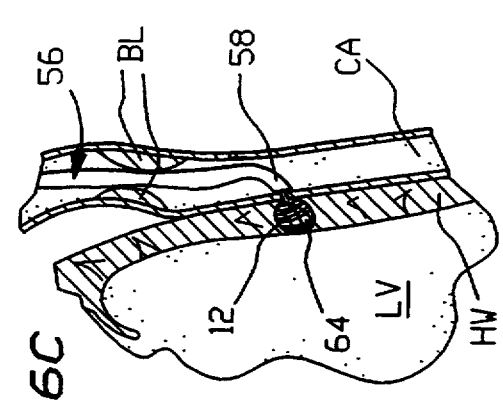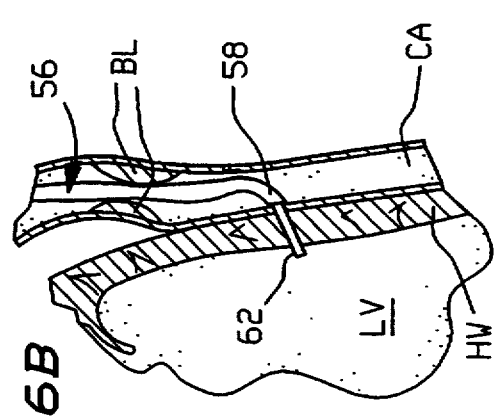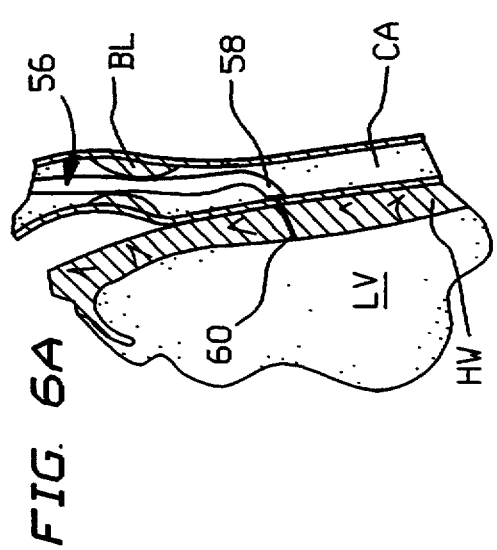
FIG. 6A  FIG. 6B  FIG. 6C

CORONARY ARTERY BY-PASS METHOD

CROSS-REFERENCE TO RELATED APPLICATION

This application is a continuation-in-part of U.S. patent application Ser. No. 08/147,072 filed Nov. 3, 1993, now allowed, which in turn was a continuation-in-part of U.S. patent application Ser. No. 07/969,747 filed Oct. 30, 1992, now U.S. Pat. No. 5,287,861.

BACKGROUND OF THE INVENTION

This invention relates to a method for effectuating a coronary artery bypass.

Coronary arteries frequently become clogged with plaque which at the very least impairs the efficiency of the heart's pumping action and can lead to heart attack. The conventional treatment for a clogged coronary artery is a coronary by-pass operation wherein one or more venous segments are inserted between the aorta and the coronary artery. The inserted venous segments or transplants by-pass the clogged portion of the coronary artery and thus provide for a free or unobstructed flow of blood to the heart.

Such conventional coronary artery by-pass surgery is expensive, time-consuming, and traumatic to the patient. Hospital stay subsequent to surgery and convalescence are prolonged.

OBJECTION OF THE INVENTION

An object of the present invention is to provide a new method for performing a coronary artery by-pass operation.

Another object of the present invention is to provide such a method which is less invasive and less traumatic to the patient than conventional by-pass surgery.

An additional object of the present invention is to provide such a method which is less expensive than conventional by-pass surgery.

A more particular object of the present invention is to provide such a method which requires no incision through the chest wall.

Yet another object of the present invention is to provide a catheter assembly for use in performing the method of the invention.

These and other objects of the present invention will be apparent from the drawings and detailed descriptions herein.

SUMMARY OF THE INVENTION

A cardiovascular treatment method comprises, in accordance with the present invention, the steps of (a) providing a stent made of a biocompatible material, (b) moving the stent in a collapsed configuration through a blood vessel of a patient's vascular system to the patient's heart, (c) inserting the stent in the patient's myocardium so that the stent extends at least partially through the myocardium and only within the myocardium, and (d) upon the disposition of the stent in the myocardium, expanding the stent from the collapsed configuration to a substantially tubular expanded configuration so that a blood flow path is formed at least partially through the myocardium.

The stent may be disposed in the myocardium so that it extends only partially through the myocardium, from a coronary artery, upstream of a vascular obstruction, or from the left ventricle of the heart. Alternatively, the stent may extend completely through the myocardium to establish a blood flow path from the left ventricle to a coronary artery, downstream of a vascular obstruction. In any case, the stent is deployed so that it extends only within the myocardium and does not protrude beyond the heart tissues, either into the left ventricle or into the coronary artery.

Where the stent extends only partially through the myocardium and thus terminates within the cardiac tissues, the stent guides blood directly into the heart tissues and particularly into cardiac vesicles which naturally occur in the myocardium. The blood is naturally distributed from the vesicles into the cardiac tissues and is collected by the veins of the heart. This function of heart tissue is known from cases in which arteries from the chest were rerouted from the chest to the heart.

Where the stent terminates within the myocardium and extends from a coronary artery, upstream of a vascular obstruction, the stent is necessarily designed to maintain its expanded form during diastole, so that blood pumped from the heart is forced into the stent and from thence into the cardiac tissues.

Where the stent terminates within the myocardium and extends from the left ventricle, the stent may be designed to collapse during systole, under the compressive forces exerted by the contracting heart muscle. In that case, blood is delivered to the myocardium during diastole: blood flows into the stent from the left ventricle as the ventricle is filling with blood. Alternatively, where the stent terminates within the myocardium and extends from the left ventricle, the stent may be designed to maintain its expanded form during systole, despite the compressive forces exerted by the contracting heart muscle. In that case, blood is forced into the stent and from thence into the cardiac tissues during heart contraction.

Where the stent traverses or extends through the myocardium, it may be designed to either collapse or remain expanded during systole. In any event, where the stent maintains its expanded configuration, it is provided with a one-way valve preventing reverse flow of blood during diastole.

According to another feature of the present invention, the step of inserting the stent into the myocardium or heart wall includes the step of ejecting the stent from a distal end of a catheter into the myocardium. The catheter is inserted along a predetermined path through the vascular system of the patient.

According to a further feature of the present invention, the step of inserting the stent into the myocardium further includes the step of forming a perforation or recess in the myocardium prior to the ejection of the stent from the catheter.

In addition, the step of inserting the stent into the myocardium may includes the steps of ejecting a collapsed inflatable balloon with the stent into the myocardium from the distal end of the catheter, the stent surrounding the balloon, and inflating the balloon and opening the stent upon ejection of the balloon and the stent into the myocardium. Generally, it is contemplated that the steps of inflating the balloon and opening the stent are performed during diastole.

The balloon and the stent may be inserted into the myocardium over a guide wire. In that case, the method further includes the step of inserting the guide wire into the perforation or recess prior to the ejection of the collapsed inflatable balloon and the stent from the distal end of the catheter.

According to feature of the present invention, the coronary bypass method further comprises the steps of inserting a distal end portion of the catheter into the perforation or recess prior to the ejection of the stent, and sensing pressure on the catheter along the distal end portion, thereby determining a thickness of the myocardium at the perforation or recess. The stent is cut from a piece of stent material so that the stent has a length corresponding to the sensed or measured thickness of the myocardium at the perforation or recess.

Other techniques for determining an optimal stent length may be used. For example, an MRI or CAT scan may be undertaken to determine myocardium thickness. In addition, such a scan may be used to determine an optimal location and angle for placing the stent. These variable can only be determined, of course, in a clinical setting, depending on the particular anatomy of the patient.

According to further features of the present invention, the formation of the perforation or recess includes the step of ejecting a needle into the myocardium from the distal end of the catheter, pushing a drill head into the myocardium from the distal end of the catheter and rotating the drill head during the step of pushing. Preferably, these steps of forming and ejecting are performed during diastole. The synchronization or coordination of the drilling, stent ejecting, and balloon inflating steps with heart action is implementable by computer.

Where the stent is disposed in the myocardium so that the stent extends only partially through the myocardium from the patient's left ventricle, the stent is inserted into the myocardium from the left ventricle. Accordingly, a distal end of the catheter is passed into the left ventricle prior to the deployment of the stent, while the stent is moved in its collapsed configuration through the catheter and into the left ventricle of the heart.

Where the stent is disposed in the myocardium so that the stent extends only partially through the myocardium from a coronary artery of the patient, the stent is inserted into the cardiac tissues from the coronary artery, preferably upstream of all vascular obstructions in the artery.

Where the stent extends from the left ventricle through the myocardium to the coronary artery, the stent is inserted from the coronary artery. The distal end of the catheter is inserted into the coronary artery prior to the deployment of the stent.

According to another feature of the present invention, the stent has an inherent spring bias tending to form the stent into the opened configuration The method then further comprises the steps of opening the stent and thereby allowing blood to flow from the left ventricle into the stent during diastole and closing the stent by heart contraction during systole.

Where the stent is provided with a one-way valve, the method further comprises the steps of maintaining the stent expanded in the opened configuration during both diastole and systole upon expansion of the stent (with the balloon or otherwise), permitting flow into the stent during systole, and blocking flow from the stent back through the valve during diastole.

A method for supplying blood to the heart comprises, in accordance with the present invention, the step of directing blood directly into the myocardium via a stent extending only partially through the myocardium and only within the myocardium. The method may include the steps of, during systole, forcing blood directly into the myocardium through the stent and, during diastole, closing a valve in the stent to block a return of blood through the stent. Alternatively, particularly where the stent extends from the left ventrical partially into the myocardium, the step of directing includes the steps of, during diastole, guiding blood into the myocardium through the stent and, during systole, closing the stent.

A cardiovascular treatment method comprises, in accordance with a particular embodiment of the present invention, the steps of (i) providing a stent made of a biocompatible material, (ii) moving the stent in a collapsed configuration through a blood vessel of a patient's vascular system to the patient's heart, (iii) upon reaching the patient's heart, disposing the stent in a wall of the patient's heart so that the stent extends only partially into the myocardium and extends only within the myocardium and does not extend into the left ventricle or the coronary artery, and (iv) upon the disposition of the stent in the myocardium, expanding the stent from the collapsed configuration to a substantially tubular permanently expanded configuration so that a flow path is formed directly into the myocardium through the stent.

As discussed above, a perforation or recess is formed in the myocardium prior to the disposition of the stent in the myocardium. The stent is inserted into the perforation or recess. To dispose the stent, a collapsed inflatable balloon is inserted with the stent into the myocardium from a distal end of a catheter. The stent surrounds the balloon. Upon insertion into the myocardium, the balloon is inflated and the stent concomitantly opened.

A method in accordance with the present invention greatly reduces the expense of coronary surgery, as well as the trauma to the patient and the convalescence required after the by-pass operation. A coronary artery by-pass operation in accordance with the present invention may be performed by a radiologist, through the vascular system of the patient. Accordingly, only one or two small incisions in the patient are necessary.

BRIEF DESCRIPTION OF THE DRAWING

FIGS. 5A–5C are partial cross-sectional views showing successive steps in the implantation of a stent in another embodiment of a method in accordance with the present invention.

FIGS. 6A–6C are partial cross-sectional views showing successive steps in the implantation of a stent in yet another embodiment of a method in accordance with the present invention.

DETAILED DESCRIPTION

Figure 1:
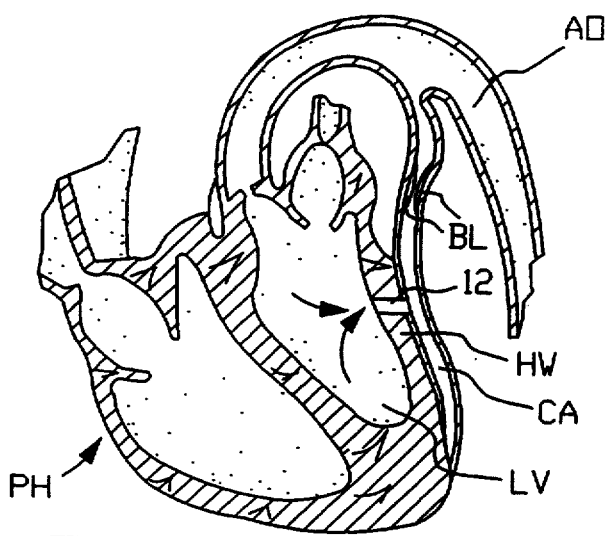
FIG. 1 is a schematic cross-sectional view of a human heart, showing a stent in the myocardium of the heart for forming a by-pass shunt between the left ventricle and a coronary artery, in accordance with the present invention.
Figure 2A:
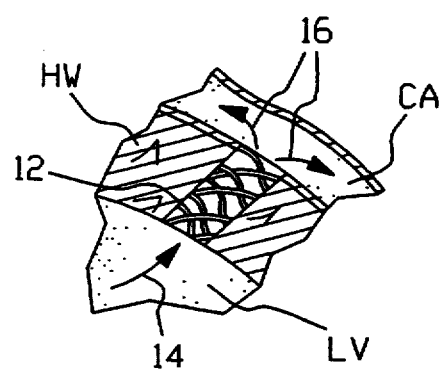
FIG. 2A is a partial cross-sectional view, on a larger scale, showing the stent of FIG. 1 in an opened or expanded configuration allowing blood flow into the coronary artery during diastole.
Figure 2B:
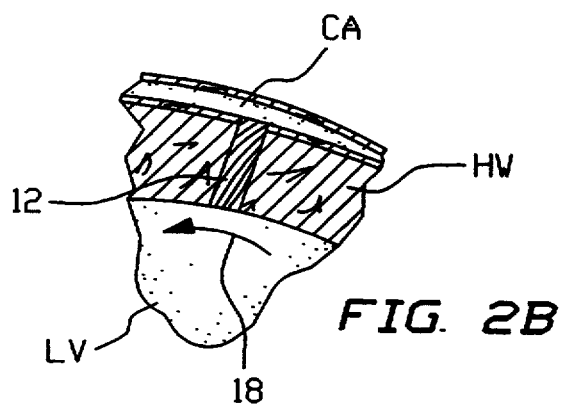
FIG. 2B is a partial cross-sectional view similar to FIG. 2A, showing the stent in an closed configuration blocking blood flow between the ventricle and the coronary artery during systole.

As illustrated in FIG. 1, a coronary artery by-pass is accomplished by disposing an alternately collapsible and expandable stent 12 in a wall HW of a patient's heart PH. Stent 12 extends from the left ventricle LV of heart PH to a clogged coronary artery CA at a point downstream of a blockage BL. Stent 12 is made of a biocompatible material and has an inherent spring bias or memory tending to form the stent into a substantially tubular opened configuration (FIG. 2A) during the relaxation of the surrounding heart muscle during the diastolic phase of a cardiac cycle. Stent 12 thus opens a passageway between ventrical LV and artery CA during diastole to allow blood to flow from the ventricle into the artery, as indicated by arrows 14 and 16 in FIG. 2A. Upon contraction of the surrounding heart muscle in the systolic phase of a cardiac cycle, stent 12 is forced closed, thus blocking or preventing blood flow between ventricle LV and coronary artery CA, as represented by an arrow 18 in FIG. 2B. FIG. 2A shows coronary artery CA in a partially collapsed configuration characteristic of diastole. Other drawing figures herein show coronary artery CA expanded for purposes of illustration simplification and clarity.

Figure 3A:
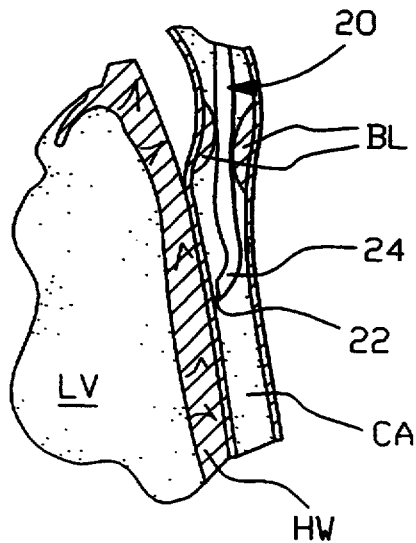
FIGS. 3A–3E are partial cross-sectional views showing successive steps in the implantation of a stent in a method in accordance with the present invention.

As illustrated in FIG. 3A, implantation or disposition of stent 12 in heart wall or myocardium HW begins with the insertion of a catheter 20 through the aorta AO (FIG. 1) and into coronary artery CA. In artery CA, catheter 20 is forced past blockage BL so that the distal tip 22 of catheter 20 is disposed in a desired location opposite heart wall HW. Catheter 20 has a steerable tip, as discussed more fully hereinafter with reference to FIG. 4, so that distal tip 22 may be controllably oriented to face wall HW, as indicated in FIG. 3A.

Figure 3D:
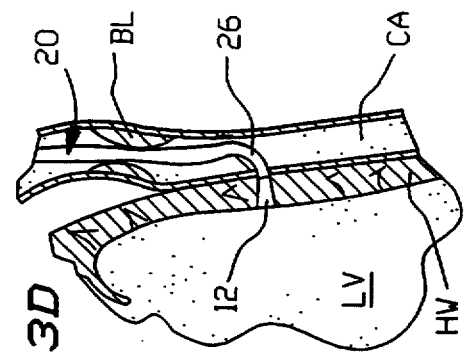
Figure 3C:
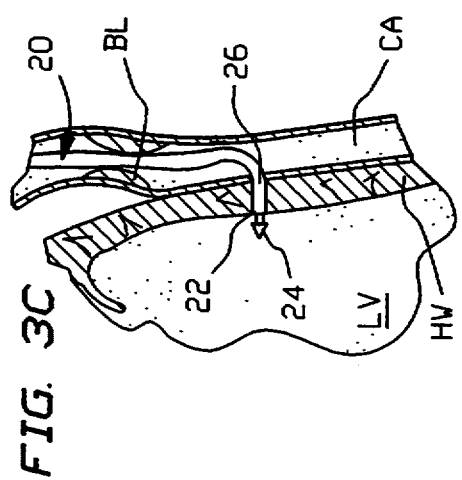
Figure 3B:
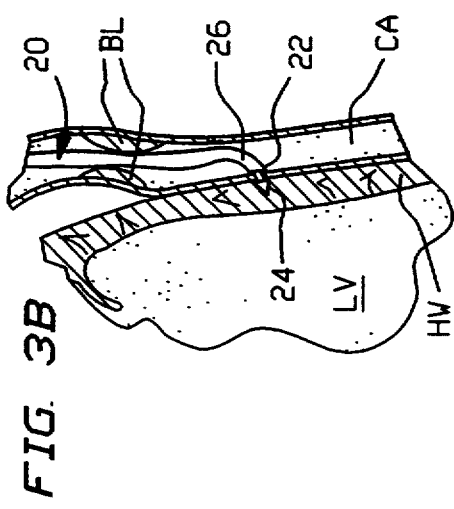

Upon a bringing of distal tip 22 into contact with wall or myocardium HW, a rotary head 24 of a surgical drill is ejected from distal tip 22, as shown in FIG. 3B. Head 24 is rotated during a pushing of catheter 20 in the distal direction, thereby forming a perforation or passage in heart wall HW. A distal end portion 26 of catheter 20 including tip 22 is inserted into the perforation in the heart wall HW during the formation of the perforation by drill head 24, as depicted in FIG. 3C.

Upon the disposition of distal end portion 26 of catheter 20 in heart wall HW, the surgical drill is withdrawn from the catheter. Stent 12 is then inserted in a collapsed configuration down catheter 20. A push rod (not shown) may be used to position stent 12 in distal end portion 26 of catheter 20 so that the stent is coextensive with heart wall HW.

Figure 3E:
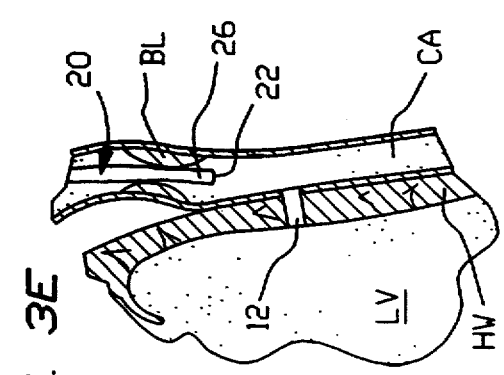

Upon the positioning of stent 12 in a collapsed configuration inside distal end portion 26 of catheter 20, catheter 20 is withdrawn from heart wall HW, while stent is maintained in position relative to heart wall. Upon the consequent ejection of stent 12 from distal tip 22 of catheter 20, as illustrated in FIG. 3D, stent 12 automatically expands from its collapsed configuration, provided that heart PH is in a diastolic phase of a cardiac cycle. Subsequently to the completed ejection of stent 12 from catheter 20, catheter 20 is withdrawn, as illustrated in FIG. 3E.

Figure 4:
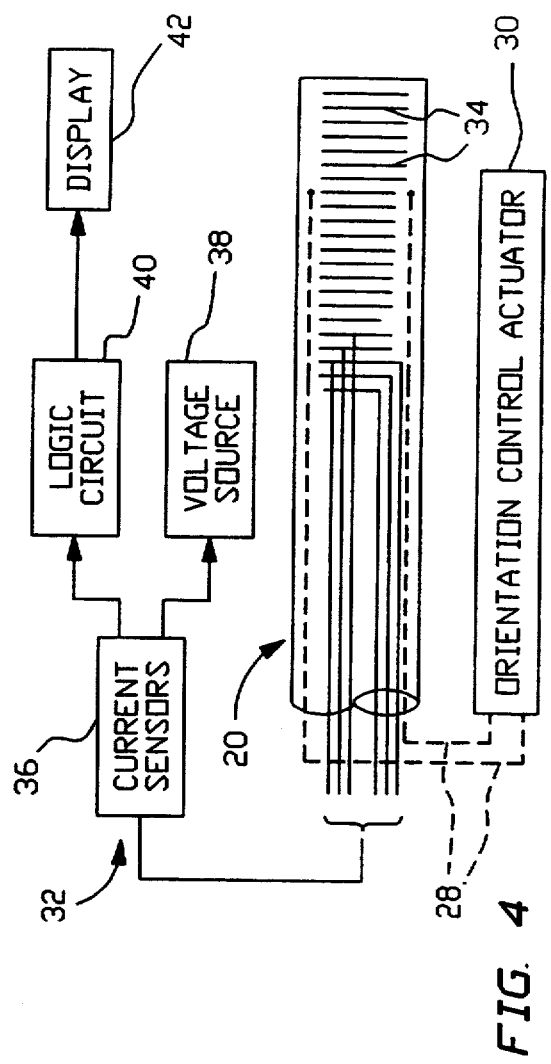
FIG. 4 is partially a block diagram and partially a side elevational view on an enlarged scale of a catheter assembly in accordance with the present invention for use in executing a method in accordance with the present invention.

FIG. 4 shows an angioplastic surgical device for use in the method described above with reference to FIGS. 3A–3E. The device includes catheter 20 insertable into aorta AO and coronary artery CA. Steering componentry including a plurality of wires 28 and an orientation control actuator 30 is connected to catheter 20 for enabling an operator to control, from outside the patient, an orientation of distal tip 22 of catheter 20 upon insertion of the catheter into the patient. A pressure sensor assembly 32 is operatively connected to catheter 20 for measuring the length of distal end portion 26 which is coextensive with heart wall HW upon completion of the catheter insertion (FIG. 3C). Pressure sensor assembly 32 may include a multiplicity of strain gauges 34 embedded in distal end portion 26, the strain gauges being connected to a current sensor array 36 and a voltage source 38. Current sensor array 36 is in turn connected to a logic circuit 40 which determines the length of that portion of catheter 20 at a distal end thereof which is subjected to increased compressive pressure especially during the systolic phase of the cardiac cycle. Circuit 40 is connected to a display 42 by means of which the thickness of the heart wall HW is communicated to a surgeon or radiologist. Stent 12 may then be customized to the patient. The length of stent 12 is matched to the measured thickness of heart wall HW by cutting the stent from a provided stent segment. Alternatively, stent 12 may be selected from a kit of different stent sizes. Of course, the cutting of stent 12 or the selection thereof may be implemented automatically by a computer operated according to a numerical control program.

As illustrated in FIGS. 5A–5C, in another procedure for disposing stent 12 in heart wall HW, a catheter 44 with a steerable distal end 46 is maneuvered to position distal end 46 in coronary artery CA and to place the end of the catheter into contact with heart wall HW. A hollow needle 48 (FIG. 5A) is then ejected from distal end 46 of catheter 44 into heart wall HW, whereupon a Seldinger wire 50 (FIG. 5B) is moved in the distal direction through catheter 44 and needle 48. Upon the projection of the distal end of wire 50 from needle 48, needle 48 is withdrawn and an auxiliary catheter 52 (FIG. 5B) is inserted through catheter 44 and over wire 50. Catheter 52 is provided with a pressure sensor assembly (not shown), as discussed hereinabove with reference to FIG. 4, for measuring the thickness of heart wall HW.

Upon the measurement of the thickness of heart wall HW, catheter 52 is withdrawn and a balloon 54 surrounded by stent 12 (not separately shown in FIG. 5C) is inserted through catheter 44 and over wire 50. Upon a positioning of balloon 54 and stent 12 inside heart wall HW, balloon 54 is inflated (FIG. 5C) to assist in an initial expansion of stent 12 in opposition to the compressive forces of the heart muscle. Upon the desired disposition of stent 12, balloon 54 and wire 50 and subsequently catheter 44 are withdrawn, leaving stent 12 in place as a coronary artery by-pass or shunt between ventricle LV and artery CA.

As illustrated in FIGS. 6A–6C, in another procedure for disposing stent 12 in heart wall HW, a catheter 56 with a steerable distal end 58 is maneuvered to position the distal end in coronary artery CA and to place the end of the catheter into contact with heart wall HW. A needle or wire 60 (FIG. 6A) is then ejected from distal end 58 of catheter 56 into heart wall HW, whereupon a series of dilating catheters 62 (FIG. 6B) of progressively increasing diameter are inserted in the distal direction through catheter 56 and over needle 60 into heart wall HW. Upon the ejection of a largest dilating catheter 62 from catheter 56 so that it traverses heart wall HW, the dilating catheter is withdrawn and a balloon 64 surrounded by stent 12 (FIG. 6C) is inserted through catheter 56 and over needle or wire 60. Upon a positioning of balloon 64 and stent 12 inside heart wall HW, balloon 64 is inflated (FIG. 6C) to assist in an initial expansion of stent 12 in opposition to the compressive forces of the heart muscle.

Upon the measurement of the thickness of heart wall HW, catheter 52 is withdrawn and a balloon 54 surrounded by stent 12 (not separately shown in FIG. 6C) is inserted through catheter 56 and over wire 50. Upon a positioning of balloon 54 and stent 12 inside heart wall HW, balloon 54 is inflated (FIG. 6C) to assist in an initial expansion of stent 12 in opposition to the compressive forces of the heart muscle. Upon the desired disposition of stent 12, balloon 54 and wire 50 and subsequently catheter 56 are withdrawn, leaving stent 12 in place as a coronary artery by-pass or shunt between ventricle LV and artery CA.

The disposition of a by-pass stent as described hereinabove may be implemented in part via a computer programmed to enable the timing of heart perforation, catheter or stent insertion, balloon inflation, and other operations so that those operations are performed only during the diastolic phase of a cardiac cycle. The programming and utilization of a computer in such a procedure will be clear to one skilled in the art from the teachings of U.S. Pat. No. 4,788,975 to Shturman et al., the disclosure of which is hereby incorporated by reference.

Figure 7A:
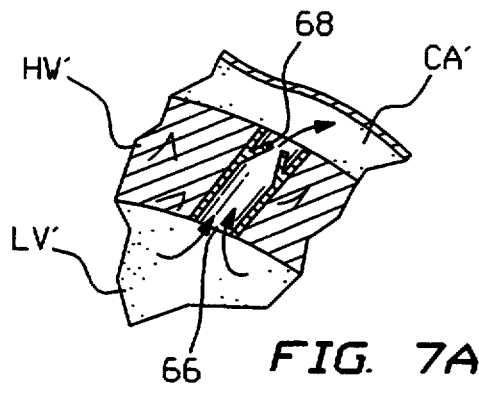
FIG. 7A is a partial cross-sectional view, similar to FIG. 2A, showing an operative configuration of another stent placed in a myocardium in accordance with the present invention, the stent having an opened one-way valve allowing blood flow into the coronary artery during systole.
Figure 7B:
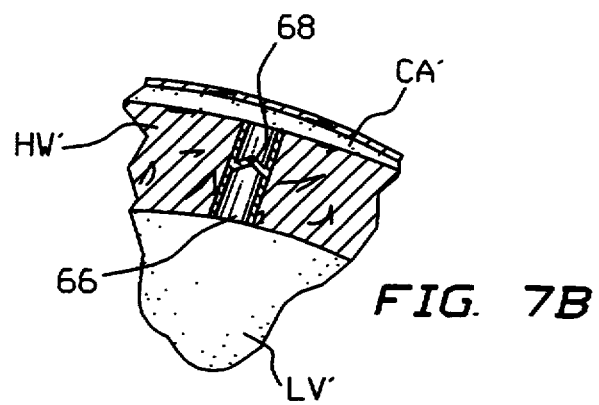
FIG. 7B is a partial cross-sectional view similar to FIG. 7A, showing the stent with the valve closed to block blood flow between from the coronary artery to the ventricle during diasystole.

As shown in FIGS. 7A and 7B, a coronary by-pass may be effectuated by disposing a stent 66 with a one-way valve 68 in a heart wall or myocardium HW' of a patient. In accordance with the embodiment of FIGS. 7A and 7B, once stent 66 is positioned in heart wall HW', the stent remains in a substantially expanded configuration. Although the stent may elastically deform under the contractive pressure of the heart muscle during systole, the stent remains opened to allow blood to pass from the patient's left ventricle LV' into the coronary artery CA'. During diastole, the blood pumped into coronary artery through shunt 66 is blocked by one-way valve 68 from returning to left ventricle LV'.

Stent 66 is installed in the patient's heart via essentially the same procedure or procedures described hereinabove for inserting stent 12. The difference between the use of stent 12 and the use of stent 66 arises from their structure. Stent 12 is designed to collapse and close during systole, while stent 66 is designed to resist the contractive pressure of the heart and to remain opened during systole to permit the flow of blood through the stent into coronary artery CA'.

Figure 8A:
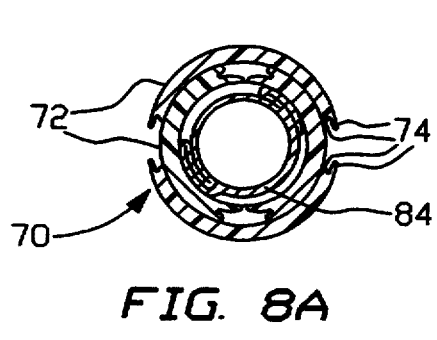
FIG. 8A is a schematic transverse cross-sectional view of another coronary by-pass stent in accordance with the present invention, showing the stent in a collapsed, pre-insertion configuration.
Figure 8B:
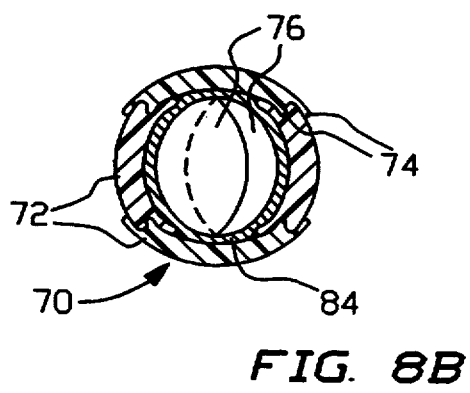
FIG. 8B is a schematic transverse cross-sectional view of the coronary by-pass stent of FIG. 9A, showing the stent in an expanded collapsed, post-insertion configuration.

As illustrated in FIGS. 8A and 8B, a stent 70 designed to resist the contractive pressure of the heart and to remain opened during systole comprises a plurality of interlocking segments 72 which overlap one another in a collapsed insertion configuration of the s tent (FIG. 8A). Along their longitudinally or axially extending edges, stent segments 72 are provided with mating or interdigitating fingers 74. In the insertion configuration, the projections are spaced from one another. Upon insertion of stent 70 into the myocardium and subsequent expansion of the stent by a balloon (not shown), fingers 74 slip into an interleaved configuration, thereby locking the stent in an opened tubular configuration which resists collapse during the systolic contractions of the heart.

Stent 70 is provided with valve flaps 76. Stent 70, like stent 12 and stent 66, is made of a biocompatible material. Valve flaps may be made of similar material in with a smaller thickness. It is to be noted that stents 66 and 70 may deform elastically during systole. Their lengths may increase during such deformation. However, they remain sufficiently open to allow the passage of blood from the left ventricle into the coronary artery.

Figure 9:
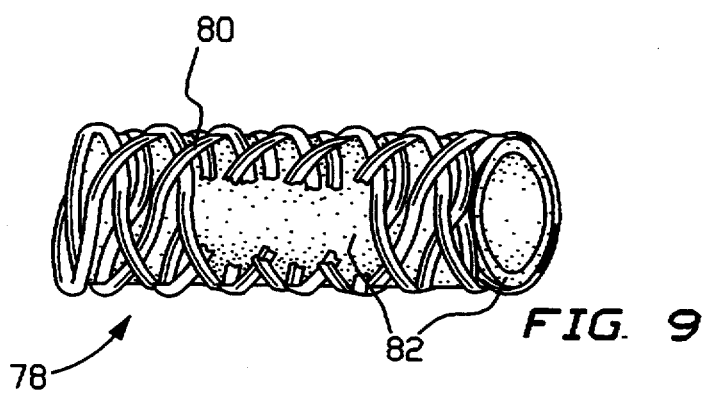
FIG. 9 is a schematic side perspective view, on an enlarged scale and partially broken away, of a modified coronary by-pass stent for use in a method in accordance with the present invention.

As illustrated in FIG. 9, a stent 78 for use in a by-pass procedure as described hereinabove includes an outer layer 80 of interwoven helical strands of biocompatible material. An inner layer 82 is a vascular graft taken from the patient prior to the by-pass operation. Vascular graft layer 82 may be connected to outer layer 80, for example, by adhesive or laser welding. FIGS. 8A and 8B also show a vascular graft layer 84 inside stent segments 72. Where a graft lining is inserted in a stent with a valve, it may be necessary to insert two vascular graft sections into the prosthetic device from opposite ends thereof.

Figure 10:
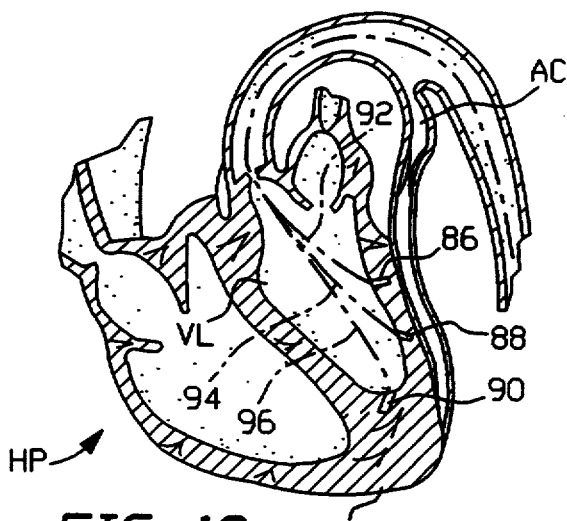
FIG. 10 is a schematic cross-sectional view of a human heart, showing a plurality of stents in the myocardium for forming a pathway for guiding blood directly into the cardiac tissues from the left ventricle, in accordance with the present invention.

As illustrated in FIG. 10, blood is supplied directly to the myocardium MYO of a patient's heart HP from a left ventricle VL via one or more stents 86, 88, and 90 extending from the left ventricle and terminating within myocardium MYO. Each stent 86, 88, and 90 thus extends only partially into myocardium MYO. Also, each stent 86, 88, and 90 is disposed entirely within myocardium MYO; none protrudes beyond myocardium MYO either into left ventricle VL or into a coronary artery AC (or, of course, into the pericardial fluid).

Figure 11:
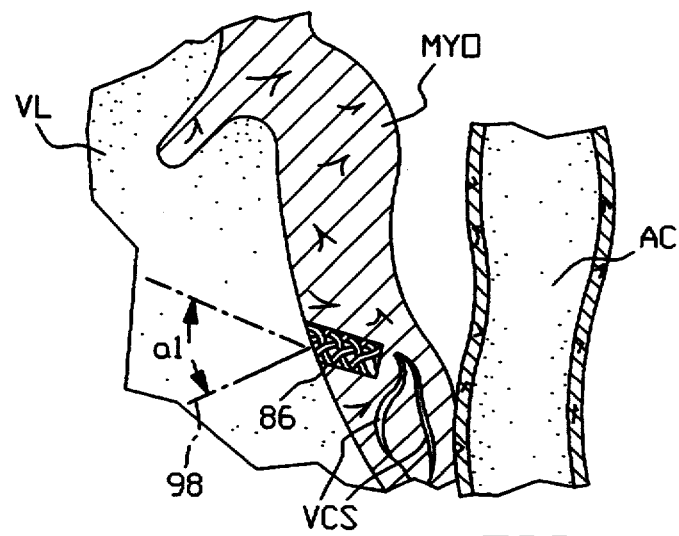
FIG. 11 is a partial cross-sectional view, on a larger scale, showing one of the stents of FIG. 10 in an expanded configuration allowing blood flow into the myocardium.

Stents 86, 88, and 90 are disposed in myocardium MYO using essentially the same technique as described above. A distal end of a catheter (not shown in FIG. 10) is inserted along a predetermined path 92, 94, 96 through the vascular system of the patient and into left ventricle VL. Upon insertion of the catheter tip into left ventricle VL and upon the orientation of the catheter tip at a predetermined angle al (FIG. 11) with respect to the perpendicular 98 to the myocardium MYO, a surgical drill (not shown) is ejected from the catheter, as described hereinabove with reference to FIG. 3B. The drill is operated to form a perforation or recess at angle al in myocardium MYO. A distal end portion of the catheter is inserted into the recess in myocardium MYO during the formation of the perforation by the drill head, as described above with reference to FIG. 3C. Upon the disposition of the distal end portion of the catheter in myocardium MYO, the surgical drill is withdrawn from the catheter. Stent 86, 88 or 90 is then inserted in a collapsed configuration down the catheter. Upon the positioning of stent 86, 88, or 90 in a collapsed configuration inside the distal end portion of the catheter (e.g. via use of a push rod), the catheter is withdrawn from myocardium MYO, while stent 86, 88, or 90 is maintained in position relative to the myocardium so that the stent extends partially into myocardium MYO and does not protrude therefrom. Upon the consequent ejection of stent 86, 88, or 90 from the distal end of the catheter, as described hereinabove with reference to FIG. 3D, stent 86, 88, or 90 automatically expands from its collapsed configuration, provided that heart HP is in a diastolic phase of a cardiac cycle. Subsequently to the completed ejection of stent 86, 88, or 90 from the catheter, the catheter may be used to place another stent 86, 88, or 90, if required.

Stents 86, 88, and 90 guide blood directly into myocardium MYO and particularly into cardiac vesicles CVS (schematically depicted in FIG. 11) which naturally occur in the myocardium. The blood is naturally distributed from vesicles VCS into cardiac tissues and is collected by the veins (not shown) of the heart.

Stents 86, 88, and 90 may be designed to collapse during systole, under the compressive forces exerted by the contracting heart muscle. In that case, blood is delivered to myocardium MYO during diastole: blood flows into stents 86, 88, and 90 from left ventricle VL as the ventricle is filling with blood. In an alternative design, stents 86, 88, and 90 maintain their expanded form during systole, despite the compressive forces exerted by the contracting heart muscle, as described hereinabove with reference to FIGS. 7A, 7B, 8A, and 8B. In that case, blood is forced into stents 86, 88, and 90 and from thence into myocardium MYO during heart contraction. Valves prevent blood from returning during diastole.

Depending on the anatomy and problems of the individual patient, a combination of the techniques described herein may constitute an optimal treatment for the patient. For example, where a plurality of stents 86, 88, and 90 are inserted from the left ventricle VL into myocardium MYO, one or two stents 86, 88, and 90 may be adapted for diastolic blood delivery, while the other(s) is designed for systolic delivery of blood. The stents have appropriate structures, as described above.

Moreover, in addition to one or more stents 86, 88, and 0 inserted from the left ventricle VL partially into myocardium MYO, one or more stents 12 or 66 may be deployed to connect left ventricle VL with coronary artery AC, as described above.

Figure 12:
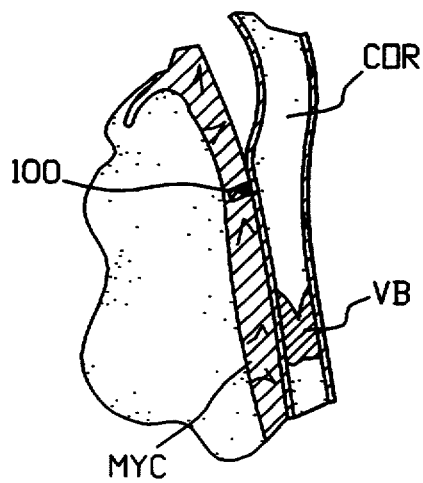
FIG. 12 is a partial cross-sectional view, similar to FIG. 11, showing another stent extending from a coronary artery partially into the myocardium for supplying oxygenated blood to the myocardium during a systolic phase of a cardiac cycle.

FIG. 12 depicts another coronary by-pass technique which may be used alone or together with one or more of the other procedures described above. A stent 100 is inserted from a coronary artery COR into the myocardium MYC of a patient's heart so that the stent extends only part way through the myocardium MYC and does not protrude from the heart wall. Stent 100 is deployed in coronary artery COR upstream of a substantially complete vascular blockage VB. In this case, stent 100 is necessarily of the diastolic type: it expands to an opened configuration during diastole to deliver blood to myocardium MYC by virtue of backflow from the aorta. Stent 100 closes during systole to prevent blood outflow through stent 100 during systole.

Although the invention has been described in terms of particular embodiments and applications, one of ordinary skill in the art, in light of this teaching, can generate additional embodiments and modifications without departing from the spirit of or exceeding the scope of the claimed invention. For example, other equivalent techniques may be used for measuring the thickness of heart wall HW or determining an appropriate length of stent 12. A "measuring rod" of a predetermined length may be inserted through the angioplastic catheter. A computer connected to a CAT-scanner, an MRI machine or other imaging device then automatically determines myocardium thickness by comparing the dimensions thereof to the known length of the "measuring rod." The computer with scanner input may be additionally used to determine optimal locations and insertion angles of multiple stents, e.g., stents 86, 88, and 90.

It is to be noted that several stents in accordance with the present invention may be disposed in the myocardium of a single heart, thereby connecting the left ventricle to one or more points along a coronary artery or to several arteries during the diastolic phase of a cardiac cycle.

Accordingly, it is to be understood that the drawings and descriptions herein are profferred by way of example to facilitate comprehension of the invention and should not be construed to limit the scope thereof.

What is claimed is:

1. A cardiovascular treatment method comprising the steps of:

provi ding a stent made of a biocompatible material;

moving said stent in a collapsed configuration through a blood vessel of a patient's vascular system to the patient's heart;

inserting said stent in the patient's myocardium so that said stent extends at least partially through the myocardium only within the myocardium; and upon the disposition of said stent in the myocardium, expanding said stent from said collapsed configuration to a substantially tubular expanded configuration so that a blood flow path is formed at least partially through the myocardium.

2. The method defined in claim 1 wherein said step of inserting includes the step of ejecting said stent from a distal end of a catheter into the myocardium, further comprising the step of inserting said catheter through the vascular system of the patient.

3. The method defined in claim 2 wherein said step of inserting further includes the step of forming a perforation or recess in the myocardium prior to said step of ejecting.

4. The method defined in claim 3 wherein said step of inserting also includes the steps of ejecting a collapsed inflatable balloon with said stent into the myocardium from said distal end of said catheter, said stent surrounding said balloon, and inflating said balloon and opening said stent upon ejection of said balloon and said stent into the myocardium.

5. The method defined in claim 4 wherein said steps of inflating and opening are performed during diastole.

6. The method defined in claim 4 wherein said balloon and said stent are inserted into the myocardium over a guide wire, further including the step of inserting said guide wire into said perforation or recess prior to the ejection of said collapsed inflatable balloon and said stent from said distal end of said catheter.

7. The method defined in claim 3, further comprising the steps of inserting a distal end portion of said catheter into said perforation or recess prior to said step of ejecting, and sensing pressure on said catheter along said distal end portion, thereby determining a thickness of the myocardium at said perforation or recess, and cutting said stent from a piece of stent material so that said stent has a length corresponding to the thickness of the myocardium at said perforation or recess.

8. The method defined in claim 3 wherein said step of forming includes the step of ejecting a needle into the myocardium from said distal end of said catheter.

9. The method defined in claim 3 wherein said step of forming includes the steps of pushing a drill head into the myocardium from said distal end of said catheter and rotating said drill head during said step of pushing.

10. The method defined in claim 3 wherein said steps of forming and ejecting are implemented during diastole.

11. The method defined in claim 3, further comprising the step of operating a computer to synchronize said steps of forming and ejecting with the rhythm of said heart.

12. The method defined in claim 1 wherein said step of inserting includes the step of disposing said stent in the myocardium so that said stent extends only partially through the myocardium from the patient's left ventricle, further comprising the step of moving said stent in said collapsed configuration into the left ventricle prior to said step of inserting.

13. The method defined in claim 1 wherein said step of inserting includes the step of disposing said stent in the myocardium so that said stent extends only partially through the myocardium from a coronary artery of the patient, further comprising the step of moving said stent in said collapsed configuration into the coronary artery prior to said step of inserting.

14. The method defined in claim 1 wherein said step of inserting includes the step of disposing said stent in the myocardium so that said stent extends from the left ventricle to the coronary artery, further comprising the step of moving said stent in said collapsed configuration into the coronary artery prior to said step of inserting.

15. The method defined in claim 1 wherein said stent has an inherent spring bias tending to form the stent into said opened configuration, further comprising the steps of opening said stent and thereby allowing blood to flow from said left ventricle into said stent during diastole and closing said stent by heart contraction during systole.

16. The method defined in claim 1 wherein said stent is provided with a one-way valve, further comprising the steps of:
maintaining said stent expanded in said opened configuration during both diastole and systole upon completion of said step of expanding;
permitting flow into said stent during systole; and
blocking flow from said stent back through said valve during diastole.

17. A method for supplying blood to the heart, comprising the step of directing blood directly into the myocardium via a stent extending only partially through the myocardium and only within the myocardium.

18. The method defined in claim 17 wherein said step of directing includes the steps of, during systole, forcing blood directly into the myocardium through said stent and, during diastole, closing a valve in said stent to block a return of blood through said stent.

19. The method defined in claim 17 wherein said step of directing includes the steps of, during diastole, guiding blood into said myocardium through said stent and, during systole, closing said stent.

20. A cardiovascular treatment method comprising the steps of:
providing a stent made of a biocompatible material;
moving said stent in a collapsed configuration through a blood vessel of a patient's vascular system to the patient's heart;
upon reaching the patient's heart, disposing said stent in a wall of the patient's heart so that said stent extends only partially into the myocardium and extends only within the myocardium and does not extend into the left ventricle or the coronary artery; and
upon the disposition of said stent in the myocardium, expanding said stent from said collapsed configuration to a substantially tubular permanently expanded configuration so that a flow path is formed directly into the myocardium through said stent.

21. The method defined in claim 20 wherein said step of disposing further includes the step of forming a perforation or recess in the myocardium prior to said step of disposing.

22. The method defined in claim 21 wherein said step of disposing also includes the steps of ejecting a collapsed inflatable balloon with said stent into the myocardium from a distal end of a catheter, said stent surrounding said balloon, and inflating said balloon and opening said stent upon ejection of said balloon and said stent into the myocardium.

23. The method defined in claim 20 wherein said step of disposing includes the steps of inserting a catheter into the coronary artery and ejecting said stent from a distal end of said catheter into the myocardium.

24. The method defined in claim 20 wherein said step of disposing includes the steps of inserting a catheter into the left ventricle and ejecting said stent from a distal end of said catheter into the myocardium.

* * * * *